(12) United States Patent
Christopher

(10) Patent No.: US 6,568,388 B2
(45) Date of Patent: *May 27, 2003

(54) METHOD AND APPARATUS FOR VENTILATION / OXYGENATION DURING GUIDED INSERTION OF AN ENDOTRACHEAL TUBE

(75) Inventor: Kent L. Christopher, Denver, CO (US)

(73) Assignee: Evergreen Medical Incorporated, Denver, CO (US)

( * ) Notice: Subject to any disclaimer, the term of this patent is extended or adjusted under 35 U.S.C. 154(b) by 133 days.

This patent is subject to a terminal disclaimer.

(21) Appl. No.: 09/767,272

(22) Filed: Jan. 22, 2001

(65) Prior Publication Data

US 2001/0012923 A1 Aug. 9, 2001

Related U.S. Application Data

(63) Continuation-in-part of application No. 09/707,350, filed on Nov. 6, 2000, which is a continuation-in-part of application No. 09/411,610, filed on Oct. 1, 1999, which is a continuation-in-part of application No. 08/974,864, filed on Nov. 20, 1997, now Pat. No. 5,964,217, which is a continuation of application No. 08/607,332, filed on Feb. 26, 1996, now Pat. No. 5,694,929.

(51) Int. Cl.[7] ............................................. A61M 16/00

(52) U.S. Cl. .............................. 128/200.26; 128/267.14

(58) Field of Search ....................... 128/200.26, 207.14, 128/207.15, 207.16

(56) References Cited

U.S. PATENT DOCUMENTS

| | | | |
|---|---|---|---|
| 1,873,160 A | | 8/1932 | Sturtevant |
| 3,683,908 A | | 8/1972 | Michael et al. |
| 3,809,079 A | | 5/1974 | Buttaravoli |
| 3,874,377 A | * | 4/1975 | Davidson ............... 128/200.26 |
| 3,948,255 A | * | 4/1976 | Davidson ............... 128/200.26 |
| 4,054,135 A | | 10/1977 | Berman |
| 4,067,331 A | | 1/1978 | Berman |
| 4,068,658 A | | 1/1978 | Berman |
| 4,069,820 A | | 1/1978 | Berman |
| 4,211,234 A | * | 7/1980 | Fisher .................... 128/200.26 |

(List continued on next page.)

OTHER PUBLICATIONS

Laerdal halping save lives, Laerdal Products Catalog, Nov. 9, 1999, 3pages, Internet article.

*Primary Examiner*—Weilun Lo
*Assistant Examiner*—Joseph F. Weiss, Jr.
(74) *Attorney, Agent, or Firm*—Dorr, Carson, Sloan & Birney, P.C.

(57) ABSTRACT

A method and apparatus for guiding insertion of an endotracheal tube into a patient's trachea simultaneously allows a continued supply of air/oxygen to be delivered into the patient's airway and lungs. A guide having a curved distal portion is inserted into the patient's mouth and hypopharynx. A second lumen extending along the guide is used to supply air/oxygen into the patient's airway and to flush carbon dioxide from the lungs. A fiber optic probe is inserted through an endotracheal tube and this assembly is advanced along the guide into the patient's airway, while ventilation continues without interruption through the second lumen. The direction of the distal tip of the fiber optic probe can be controlled by the physician. This allows the physician to carefully guide the fiber optic probe and endotracheal tube to a position past the larynx while ventilation continues. After the distal end of the fiber optic probe has guided the endotracheal tube past the larynx and into the trachea, the guide and mask are withdrawn over the fiber optic probe. The fiber optic probe can used to monitor the position of the distal end of the endotracheal tube during this step to ensure that it remains in position. The fiber optic probe is then removed from within the endotracheal tube. The cuff on the endotracheal tube is inflated and a ventilator is connected to the proximal end of the endotracheal tube to ventilate the patient.

17 Claims, 13 Drawing Sheets

U.S. PATENT DOCUMENTS

| | | | | |
|---|---|---|---|---|
| 4,231,365 A | * | 11/1980 | Scarberry | 128/207.15 |
| 4,256,099 A | | 3/1981 | Dryden | |
| 4,369,991 A | * | 1/1983 | Linder | 285/38 |
| 4,497,318 A | | 2/1985 | Donmichael | |
| 4,559,940 A | * | 12/1985 | McGinnis | 128/206.26 |
| 4,580,556 A | | 4/1986 | Kondur | |
| 4,593,690 A | * | 6/1986 | Sheridan et al. | 128/207.15 |
| 4,774,941 A | | 10/1988 | Cook | |
| 4,809,693 A | * | 3/1989 | Rangoni et al. | 128/207.16 |
| 4,811,730 A | * | 3/1989 | Milano | 128/203.11 |
| 4,848,331 A | | 7/1989 | Northway-Meyer | |
| 4,892,095 A | * | 1/1990 | Nakhgevany | 128/207.14 |
| 5,050,615 A | * | 9/1991 | Malkamaki | 600/632 |
| 5,197,463 A | | 3/1993 | Jeshuran | |
| 5,203,320 A | | 4/1993 | Augustine | |
| 5,253,643 A | * | 10/1993 | Price | 128/207.14 |
| 5,257,620 A | * | 11/1993 | Schermerhorn | 128/200.26 |
| 5,261,392 A | * | 11/1993 | Wu | 128/200.26 |
| 5,295,478 A | | 3/1994 | Baldwin | |
| 5,339,805 A | | 8/1994 | Parker | |
| 5,339,808 A | * | 8/1994 | Don Michael | 128/207.15 |
| 5,348,000 A | | 9/1994 | Teves | |
| 5,400,771 A | * | 3/1995 | Pirak et al. | 128/200.26 |
| 5,477,851 A | | 12/1995 | Callaghan et al. | |
| 5,513,627 A | * | 5/1996 | Flam | 128/200.26 |
| 5,588,424 A | * | 12/1996 | Insler et al. | 128/207.15 |
| 5,607,386 A | | 3/1997 | Flam | |
| RE35,531 E | | 6/1997 | Callaghan et al. | |
| 5,636,625 A | | 6/1997 | Miyagi et al. | |
| 5,645,519 A | | 7/1997 | Lee et al. | |
| 5,682,880 A | * | 11/1997 | Brain | 128/207.15 |
| 5,694,929 A | | 12/1997 | Christopher | |
| 5,720,275 A | * | 2/1998 | Patil et al. | 128/200.26 |
| 5,840,013 A | | 11/1998 | Lee et al. | |
| 5,921,917 A | | 7/1999 | Barthel et al. | |
| 5,937,858 A | * | 8/1999 | Connell | 128/207.14 |
| 5,941,816 A | | 8/1999 | Barthel et al. | |
| 5,954,050 A | | 9/1999 | Christopher | |
| 5,964,217 A | | 10/1999 | Christopher | |
| 6,004,263 A | | 12/1999 | Nakaichi et al. | |
| 6,079,409 A | * | 6/2000 | Brain | 128/200.26 |
| 6,189,533 B1 | * | 2/2001 | Simon et al. | 128/207.14 |
| 6,415,787 B1 | * | 7/2002 | Boussignac | 128/200.26 |

* cited by examiner

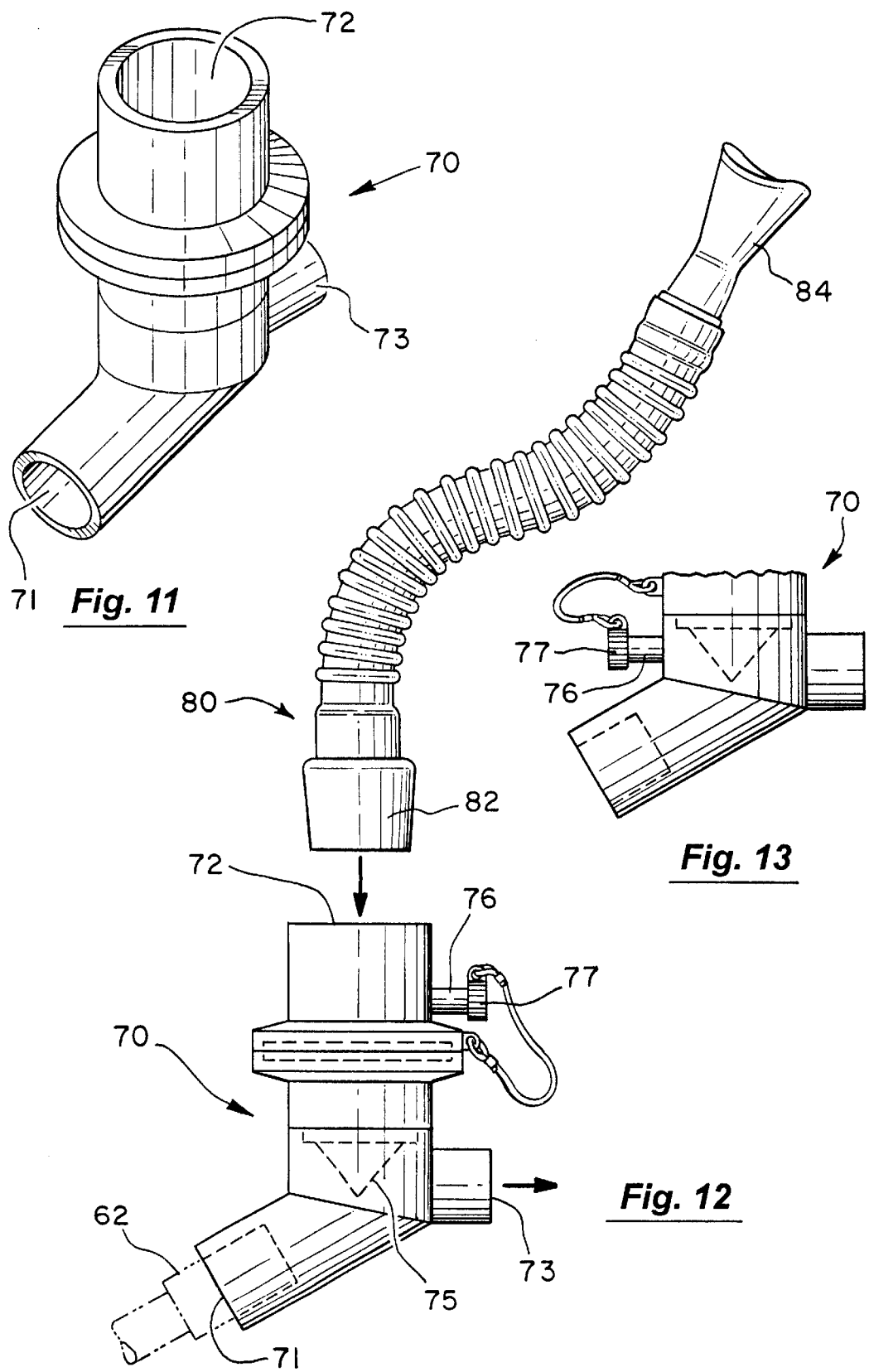

METHOD AND APPARATUS FOR VENTILATION / OXYGENATION DURING GUIDED INSERTION OF AN ENDOTRACHEAL TUBE

RELATED APPLICATIONS

The present application is a continuation-in-part of the Applicant's U.S. patent application Ser. No. 09/707,350, filed on Nov. 6, 2000, which is a continuation-in-part of U.S. patent application Ser. No. 09/411,610, filed on Oct. 1, 1999, which is a continuation-in-part of U.S. patent application Ser. No. 08/974,864, filed on Nov. 20, 1997, now U.S. Pat. No. 5,964,217, issued on Oct. 12, 1999, which is a continuation of U.S. patent application Ser. No. 08/607,332, filed on Feb. 26, 1996, now U.S. Pat. No. 5,694,929, issued on Dec. 9, 1997.

BACKGROUND OF THE INVENTION

1. Field of the Invention

The present invention relates generally to the field of respiratory devices and methods. More specifically, the present invention discloses a method and apparatus for guiding insertion of an endotracheal tube while the patient continues to receive ventilation or cardiopulmonary resuscitation.

2. Statement of the Problem

In emergency situations involving cardiopulmonary patients or other patients with compromised or arrested breathing, an oral airway is first inserted into the patient's mouth. A face mask is then placed over the patient's mouth and nose. The face mask is connected to an inflatable bag to maintain at least minimal oxygen flow to the lungs in the short term. This process is sometimes referred to as "bagging" the patient. It is suitable for initially stabilizing the patient. In order to breathe more effectively for the patient during cardiopulmonary resuscitation, and to prevent aspiration of stomach contents, an endotracheal tube (or ET tube) is placed into the trachea. Longer-term care usually requires attaching the patient to a ventilator (e.g., by means of the endotracheal tube). The transition from face mask to breathing through the endotracheal tube can be dangerous if insertion of the endotracheal tube takes too long, because the mask and oral airway must be removed and the flow of air/oxygen is interrupted while the endotracheal tube is inserted through the patient's mouth.

The typical conventional approach to making this transition involves discontinuing resuscitation and completely removing the mask and oral airway to expose the mouth. The physician inserts a rigid laryngoscope blade into the patient's mouth to ensure that the patient's airway is open, and then attempts to insert the endotracheal tube through the patient's mouth and into the trachea in the conventional manner. This may require a significant amount of time, particularly if the patient is less than completely cooperative and relaxed, or if the patient's airway has suffered trauma, or the tongue has fallen back to close the airway. The patient may not be breathing during this time, or may not be breathing sufficiently to maintain adequate blood oxygen levels. If the transition process takes more than a few seconds, the physician must temporarily abandon the effort and return to resuscitation by reinserting the oral airway and replacing the face mask. The transition process may have to be repeated several times before the endotracheal tube is successfully installed. In addition, the speed with which the transition process must be completed increases the chances of a mistake being made or unnecessary injury to the patient during the intubation procedure.

Endotracheal tubes are also used in semi-emergency situations to ventilate patients with respiratory failure who may be conscious or semi-conscious. The conventional approach requires the patient to lie still while the physician inserts a rigid laryngoscope blade into the patient's mouth and trachea. Delivery of ventilation and/or oxygen is also interrupted during this period. The endotracheal tube is then inserted into place while the laryngoscope blade keeps the patient's airway open. Successful intubation depends on the patient being cooperative and completely relaxed, which unfortunately is often not the case. Even with a cooperative patient, intubation is very uncomfortable and can cause the patient to panic due to the difficulty in breathing during the procedure. This procedure can also result in a choking or gagging response that can cause the patient to regurgitate and aspirate contents from the stomach. One conventional response to these shortcomings has been to sedate the patient during intubation. Tranquilizers make the patient more cooperative and less likely to choke during intubation, but also tend to suppress the patient's breathing and blood pressure. These side effects may be unacceptable when dealing with a patient who already suffers from shallow or irregular breathing or depressed blood pressure. Therefore, a need exists for an improved device to guide insertion of an endotracheal tube and ensure that the patient's airway is open, and that also allows the patient to continue to receive air/oxygen during the insertion process.

A wide variety of devices that combine face masks with tubes for ventilation (e.g., endotracheal tubes) have been used in the past, including the following:

| Inventor | Patent No. | Issue Date |
|---|---|---|
| Teves | 5,348,000 | Sep. 20, 1994 |
| Don Michael | 5,339,808 | Aug. 23, 1994 |
| Jeshuran | 5,197,463 | Mar. 20, 1993 |
| Northway-Meyer | 4,848,331 | Jul. 18, 1989 |
| Kondur | 4,580,556 | Apr. 8, 1986 |
| Donmichael | 4,497,318 | Feb. 5, 1985 |
| Dryden | 4,256,099 | Mar. 17, 1981 |
| Buttaravoli | 3,809,079 | May 7, 1974 |
| Michael et al. | 3,683,908 | Aug. 15, 1972 |

Teves discloses a system for dispensing oxygen or anesthesia via an interchangeable face mask and nasal catheter.

Don Michael discloses a endotracheal-esophageal intubation device that includes a face mask (see, FIG. 2 of the Don Michael patent).

Jeshuran shows an anesthesia mask 28 that is initially placed over the patient's mouth and nose as shown in FIG. 7 of the Jeshuran patent. A fiber optic 40 is inserted through an endotracheal tube, and then through an opening in a two-piece core 84, 86, as shown in FIG. 9 of the Jeshuran patent. The fiber optic 40 is advanced into the trachea. The head 96 is then unscrewed and the core segments 84, 86 are disassembled to allow the endotracheal tube to be inserted through the mask, as shown in FIG. 2 of the Jeshuran patent. The fiber optic 40 serves as a guide for insertion of the endotracheal tube 46. The fiber optic 40 is then withdrawn and the endotracheal tube cuff 136 is inflated, as shown in FIG. 8 of the Jeshuran patent. However, Jeshuran does not show a curved guide to direct insertion of the fiber optic probe. The physician is faced with the problem of navigating the fiber optic probe past the patient's tongue and along the airway.

Northway-Meyer discloses a device for pulmonary ventilation concurrent with fiber optic examination of the respiratory tract and tracheal intubation. In particular, Northway-Meyer discloses a face mask with a plurality of ports for ventilation and intubation of the patient, and curved guide for advancing an endotracheal tube.

Kondur discloses another example of an adapter 10 that allows insertion of an endotracheal tube 40 through the face mask 50 and nose of the patient. Here again, no curved guide is provided.

Donmichael discloses an esophageal obturator for blocking aspiration of stomach fluids while the face mask is being used for ventilating the lungs.

Dryden discloses a two-tube resuscitation system. One tube is used to supply air to the trachea, while the other tube is used for aspiration or administering medication.

Buttaravoli discloses a resuscitator having a face mask 11 with a curved tube 15 for supplying air to the patient's airway.

Michael et al. disclose an apparatus for sealing a patient's esophagus and providing artificial respiration. The apparatus includes a mouth shield 14 and a curved main tube 10.

In addition, the prior art includes several references involving intubating pharyngeal airways that have a curved tubular member, including the following:

| Inventor  | Patent No. | Issue Date     |
| --------- | ---------- | -------------- |
| Parker    | 5,339,805  | Aug. 23, 1994  |
| Parker    | 5,743,254  | Apr. 28, 1998  |
| Augustine | 5,203,320  | Apr. 20, 1993  |
| Berman    | 4,069,820  | Jan. 24, 1978  |
| Berman    | 4,068,658  | Jan. 17, 1978  |
| Berman    | 4,067,331  | Jan. 10, 1978  |
| Berman    | 4,054,135  | Oct. 18, 1977  |

The Parker '805 patent discloses a curved guide for intubation of a patient's trachea or suctioning of the hypopharynx or esophagus.

The Parker '254 patent discloses a curved guide for orotracheal intubation.

Augustine discloses a tracheal intubation guide with a curved forward end.

The Berman patents show an intubating pharyngeal airway having a side access for passage of a tube. The side opening can be expanded or closed by means of either a hinge on the opposite side wall of the tube or by a cap.

Finally, the prior art includes several examples in which supplemental air/oxygen is supplied through a secondary lumen extending along a laryngoscope or ventilating airway, including the following:

| Inventor     | Patent No. | Issue Date     |
| ------------ | ---------- | -------------- |
| Ha           | 6,106,458  | Aug. 22, 2000  |
| Hete et al.  | 6,102,042  | Aug. 15, 2000  |
| Kurtis       | 5,509,408  | Apr. 23, 1996  |
| Bartlett     | 4,947,896  | Aug. 14, 1990  |
| Watson et al.| 4,446,864  | May 8, 1984    |
| May          | 4,126,127  | Nov. 21, 1978  |

Ha discloses an anesthetic laryngoscope with a handle and a blade having an observation light and a oxygen supply tube mounted thereon.

Hete et al. disclose an insufflation system that includes a first tube that inserts into a patient's airway to provide a primary flow of gas from a ventilator. A second, insufflation catheter is provided within the first tube for delivering a flow of insufflation gas to the patient.

Kurtis discloses a neonatal resuscitation device that includes an endotracheal tube with lumens that can be used either for suction or ventilation.

Bartlett discloses a laryngoscope with a handle and a blade having a suction tube and a plurality of other channels extending along its length.

Watson et al. disclose an emergency ventilation tube having coaxial tubular members for ventilating the patient and inflating a cuff at the distal end of the ventilation tube. The device can also be used in conjunction with a face mask.

May discloses a laryngoscope blade having conduits for suction and ventilation, and a light source for illumination.

3. Solution to the Problem

None of the prior art references discussed above show an intubation guide that allows continued ventilation of the patient via a second lumen while the endotracheal tube is being inserted into the patient's airway. The guide may also be used in conjunction with a face mask for initial resuscitation of the patient. During intubation, a fiber optic probe is inserted through the endotracheal tube and this assembly is advanced along the guide. The curved distal portion of the guide directs the fiber optic probe and endotracheal tube along the patient's airway while ventilation continues. After the distal end of the fiber optic probe has guided the endotracheal tube past the larynx and into the trachea, the guide and mask are withdrawn over the fiber optic probe. The fiber optic probe can used to monitor the position of the distal end of the endotracheal tube during this step to ensure that it remains in the proper position. The fiber optic probe can then be withdrawn and the endotracheal tube is be connected to an external ventilator. Alternatively, the guide can be left in place to serve as a bite guard.

This system allows the endotracheal tube to be inserted and connected to a ventilator without interrupting the flow of air/oxygen to the patient's lungs. In addition, the curved guide greatly simplifies insertion of the fiber optic probe and endotracheal tube by providing direction and maintaining an open passageway past the patient's tongue and into the hypopharynx.

The supplemental flow of air/oxygen through the second lumen helps to maintain the patient's blood oxygen level and flushes carbon dioxide from the patient's lungs during intubation. Optionally, a third lumen extending along the guide can be used to monitor the carbon dioxide level within the patient's airway.

SUMMARY OF THE INVENTION

This invention provides a method and apparatus for guiding insertion of an endotracheal tube into a patient's trachea while continuing to supply air/oxygen into the patient's airway and lungs. A guide having a curved distal portion is inserted into the patient's mouth and hypopharynx. A second lumen extending along the guide is used to supply air or oxygen into the patient's airway and to flush carbon dioxide from the lungs. A fiber optic probe is inserted through an endotracheal tube and this assembly is advanced along the guide into the patient's airway, while ventilation continues without interruption through the second lumen. The direction of the distal tip of the fiber optic probe can be controlled by the physician. This allows the physician to carefully guide the fiber optic probe and endotracheal tube to a position past the larynx while ventilation continues.

After the distal end of the fiber optic probe has guided the endotracheal tube past the larynx and into the trachea, the guide and mask are withdrawn over the fiber optic probe. The fiber optic probe can used to monitor the position of the distal end of the endotracheal tube during this step to ensure that it remains in position. The fiber optic probe is then removed from within the endotracheal tube. The cuff on the endotracheal tube is inflated and a ventilator is connected to the proximal end of the endotracheal tube to ventilate the patient.

A primary object of the present invention is to provide a method and apparatus for guiding insertion of an endotracheal tube that does not require interruption of the ventilation process.

Another object of the present invention is to provide a method and apparatus for improving insertion of an endotracheal tube by helping to keep the patient's airway open, and also allowing the physician to guide the insertion process via the fiber optic probe.

Another object of the present invention is to provide a method and apparatus for guiding insertion of an endotracheal tube that lessens the risk of injury and reduces patient discomfort.

Another object of the present invention is to achieve oxygenation and ventilation of the patient while the hands of the healthcare provider remain free to perform intubation.

Another object of the present invention is to allow for monitoring of gases (e.g., carbon dioxide) in the patient's airway.

Yet another object of the present invention is to provide a method and apparatus for instilling local anesthetic into the patient's airway prior to, or during insertion of the endotracheal tube.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 11 is a front perspective view of a removable resuscitation attachment 70 that can be connected to the ventilation port 62 of the face mask 20.

FIG. 12 is a side view of the resuscitation attachment 70 and flexible tubing 80.

FIG. 13 is a detail side view of an alternative embodiment of the resuscitation attachment 70 in which the location of the oxygen port 76 has been placed below the filter and one-way valve.

DETAILED DESCRIPTION OF THE INVENTION

Figure 1:
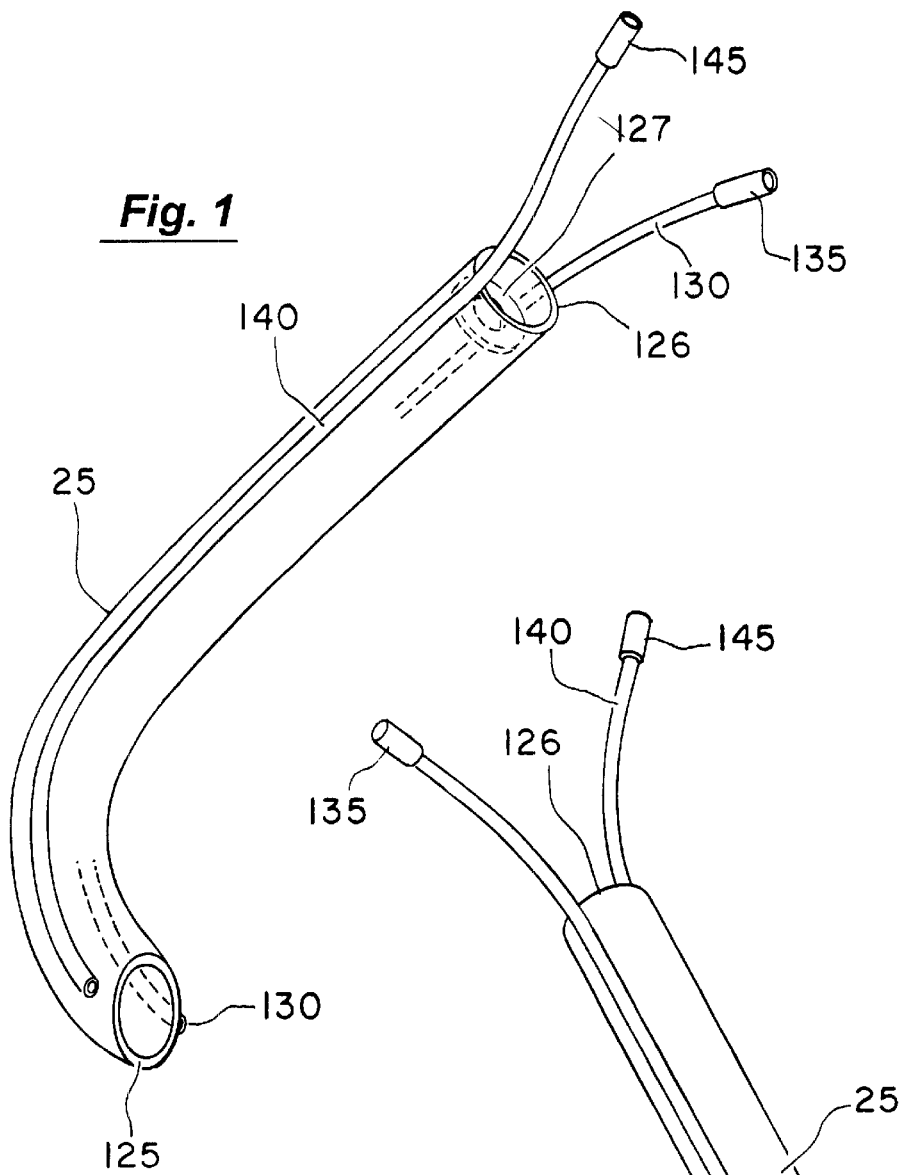
FIG. 1 is a front perspective view of the guide assembly.
Figure 2:
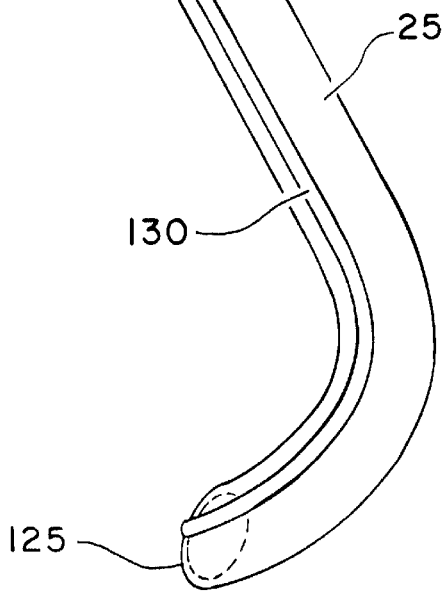
FIG. 2 is a rear perspective view of the guide assembly corresponding to FIG. 1.
Figure 3:
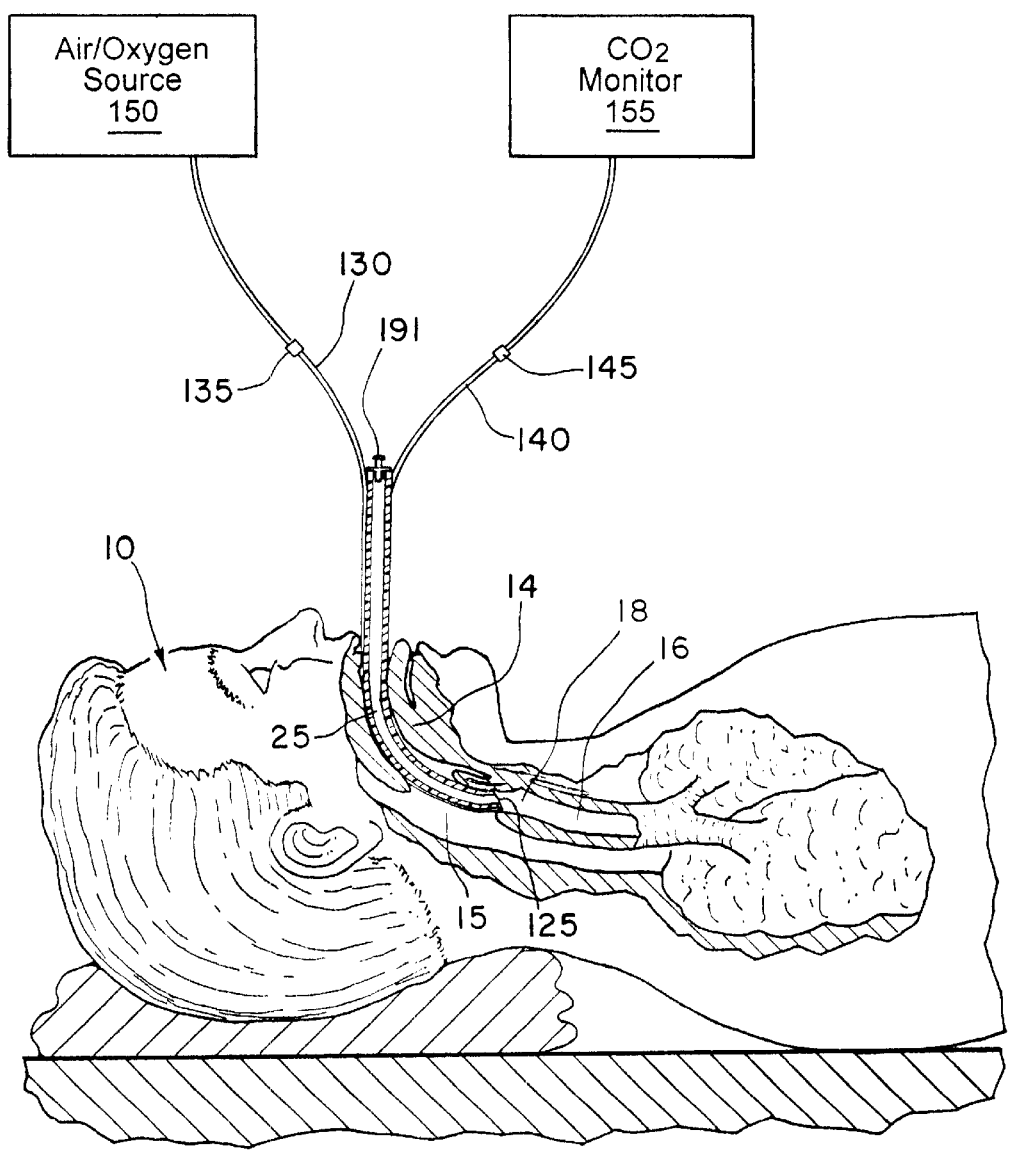
FIG. 3 is a cross-sectional view of the mouth and airway of a patient after the guide assembly has been inserted into the patient's mouth, over the tongue 14, and into the hypopharynx 15.

Turning to FIGS. 1 and 2, front and rear perspective views are provided showing the guide assembly 25 used in the present invention. FIG. 3 is a corresponding cross-sectional view of the mouth and airway of a patient after the guide assembly has been inserted into the patient's mouth and hypopharynx 15. The guide 25 is generally tubular and has a curved distal portion to follow the profile of a typical patient's airway through the mouth, over the tongue 14, and into the hypopharynx 15 just above the opening to the trachea 16. Although the guide 25 is generally J-shaped, it may be necessary to provide a variety of guides with different dimensions and profiles to accommodate variations in the size and shape of patient airways. Ideally, the guide 25 should extend from the patient's mouth and through the hypopharynx with its distal end 125 immediately above the opening to the larynx. In particular, the guide 25 is shaped to prevent the patient's tongue 14 and collapsible pharynx from obstructing access to the trachea 16, while also defining a channel for later insertion of an endotracheal tube.

The guide 25 is typically made of plastic with sufficient strength and rigidity to keep the patient's teeth apart and prevent the patient from biting down on the endotracheal tube. In addition, the guide 25 should have a relatively low coefficient of friction to minimize irritation to the lining of mouth and trachea and to minimize resistance to insertion of the endotracheal tube along the guide. Friction can be further reduced by applying a slippery coating to both the exterior and interior surfaces of the guide 25. A slippery coating can also be applied to the endotracheal tube to minimize friction between the endotracheal tube and the guide. The distal end 125 of the guide 25 can be beveled to ease insertion. The tip of the bevel should preferably be located on the posterior side of the guide 25 as shown in the drawings.

The guide 25 is equipped with a small second lumen 130 bonded to the exterior of the guide 25 that extends along the length of the guide 25. The second lumen 130 delivers a flow of air/oxygen for supplemental ventilation of the patient. Preferably, this lumen 130 extends to the distal tip 125 of the guide 25 so that this supplemental air/oxygen can be delivered near the opening to the larynx to flow through the opening between the vocal cords and into the patient's lungs.

The second lumen 130 can have any radial position relative to the central longitudinal axis of the guide. However, it is easier to align the flow exiting the second lumen 130 with the opening between the vocal cords if the second lumen 130 extends along the lateral portion of the guide 25 (e.g., at the 3 o'clock or 9 o'clock positions). In contrast, the second lumen 130 might tend to become obstructed with mucous or secretions if it is placed along the posterior or anterior portions of the guide 25. In addition, the tip of the second lumen 130 or the flow of air/oxygen might irritate the patient's airway in these configurations.

As shown in FIGS. 1 and 2, the second lumen 130 can be a tube bonded to the exterior of the guide 25 so that it does not interfere with the endotracheal tube 40 as it is advanced along the interior passageway of the guide 25. Alternatively, the lumen 250 can be placed within the guide 25 or formed as a conduit in the wall of the guide 25. The lumen should have a diameter (or cross-sectional area) sufficient to support of flow rate of approximately 1 to 20 liters per minute with minimal back pressure.

A standard connector 135 on the proximal end of the second lumen 130 allows it to be removably attached to a conventional air/oxygen source 150, as illustrated in FIG. 3. For example, the second lumen 130 can be connected to an oxygen line of the type commonly found in hospitals and other clinical settings. Alternatively, the second lumen 130 can be connected to a portable oxygen source or a ventilator, such as an anesthesia ventilator. Here again, a flow rate of approximately 1 to 20 liters per minute is preferable. For example, the flow can be provided on a continuous basis, in periodic pulses, or in a waveform simulating the patient's nature respiratory cycle. The flow of air/oxygen increases diffusion oxygenation within the alveoli to boost the patient's blood oxygen level, and also serves to flush carbon dioxide from the patient's lungs and airway. In addition, if the flow rate of oxygen supplied through the second lumen 130 is sufficiently high, oxygen will accumulate in the patient's upper airway and create a reservoir of oxygen that enhances the effectiveness of the patient's natural respiration.

Optionally, the guide 25 can be equipped with a third lumen 140 to sample and measure the chemical composition of gas in the patient's airway. For example, the third lumen can be used to monitor the concentration of carbon dioxide in the patient's airway. As shown in FIG. 1, the third lumen 140 extends along the lateral portion of the guide 25 opposite from the second lumen 130 to minimize the affect of the air/oxygen supplied via the second lumen 130 on the accuracy of the carbon dioxide measurement. In the preferred embodiment depicted in FIG. 1, the distal end of the third lumen 140 terminates short of the distal end 125 of the guide 25 to further enhance the accuracy of the carbon dioxide measurement.

The carbon dioxide concentration in a patient's airway can vary widely over the patient's respiratory cycle. Due to the physiological dead space in the patient's airway, measurements taken at the end of exhalation in the respiratory cycle (i.e., end-tidal measurements) tend to most accurately reflect the concentration of carbon dioxide in the lungs, and therefore most accurately reflect the concentration of carbon dioxide in the patient's blood stream.

Returning to FIG. 3, the proximal end of the third lumen 140 is fitted with a connector 145 so that a carbon dioxide monitor 155 can periodical sample gas from the patient's airway via the third lumen 140 for analysis. As with the second lumen 130, the third lumen 140 can be a small tube bonded to the exterior of the guide 25, as shown in the accompanying drawings. Alternatively, it can be bonded to the interior of the guide 25 or formed as a conduit in the wall of the guide 25.

If necessary, the guide 25 can be equipped with additional lumens for other purposes. For example, a suction tube can be used to suction secretions from the patient's mouth and airway as the guide 25 is advanced. Alternatively a syringe 55 containing a local anesthetic (e.g., lidocaine or xylocaine) can be connected to the proximal end of an ancillary lumen to squirt anesthetic as the guide 25 is inserted through the patient's mouth and into the hypopharynx 15. If squirted with sufficient force, the anesthetic can be carried as far as the larynx 18 to deaden any discomfort associated with insertion of the endotracheal tube 40. The main lumen of the guide 25 can also be used for suctioning secretions from the patient's mouth and airway, if necessary.

During and after insertion of the guide 25, air/oxygen is supplied through the second lumen 130 to maintain the patient, as shown in FIG. 3. If necessary, a cap 191 can be temporarily inserted into the proximal end of the guide 25 to instill topical anesthetic through the guide 25. This supplemental flow of air/oxygen gives the healthcare provider extra time to insert the endotracheal tube 40 (as described below), verify its location, and connect the patient to a ventilator.

Figure 4:
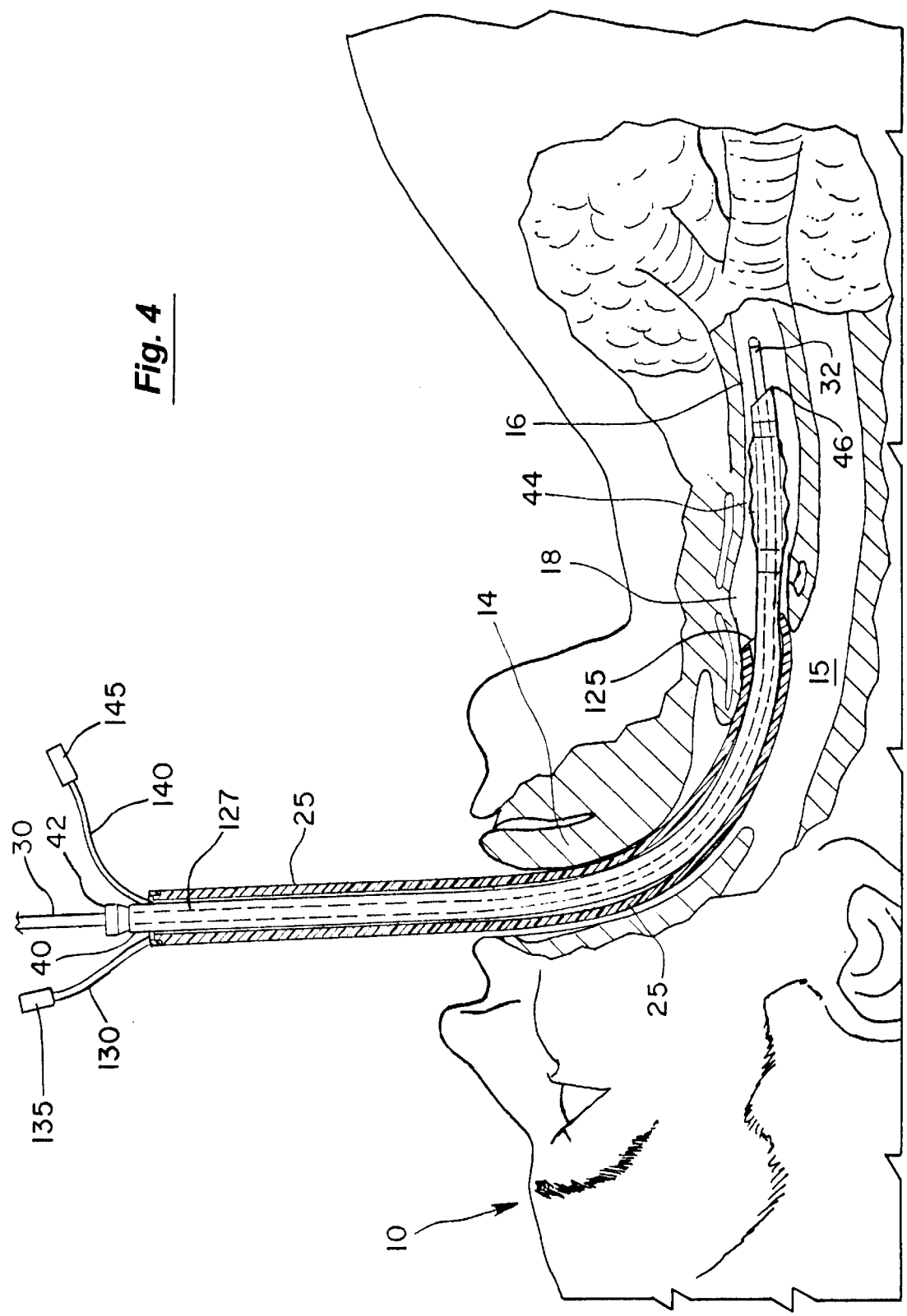
FIG. 4 is a cross-sectional view of the mouth and airway of the patient corresponding to FIG. 3 after the fiber optic probe 30 and endotracheal tube 40 have been advanced along the guide 25 to a position below the larynx 18.

An endotracheal tube 40 is inserted over a fiber optic probe 30 (e.g., the fiber optic probe of a conventional endoscope). The cap 191 is removed from the guide 25. The fiber optic probe 30 and endotracheal tube 40 are then inserted along the guide 25 to a position within the trachea 16 past the larynx 18 while the flow of air/oxygen continues through the second lumen 130, as illustrated in FIG. 4. In the preferred embodiment, an annular ring 127 within the proximal end of the guide 25 forms a loose seal around the endotracheal tube 40 to help prevent potentially contaminated respiratory secretions from being sprayed up at the physician between the guide 25 and the endotracheal tube 40. Likewise, the endotracheal tube cap 42 also helps to prevent potentially contaminated respiratory secretions from reaching the physician.

The fiber optic probe 30 allows the physician to view within the patient's mouth and trachea 16 during insertion. The physician can also remotely manipulate the direction of the probe tip 32 to control the direction of the fiber optic probe 30. This minimizes patient discomfort and risk of injury to the patient. The small size of the fiber optic probe 30 also allows the physician to thread the fiber optic probe 30 through relatively constricted areas within the airway, such as the larynx 18. Most importantly, the fiber optic probe 30 and endotracheal tube 40 do not interfere with ongoing ventilation of the patient via the second lumen 130.

Figure 6:
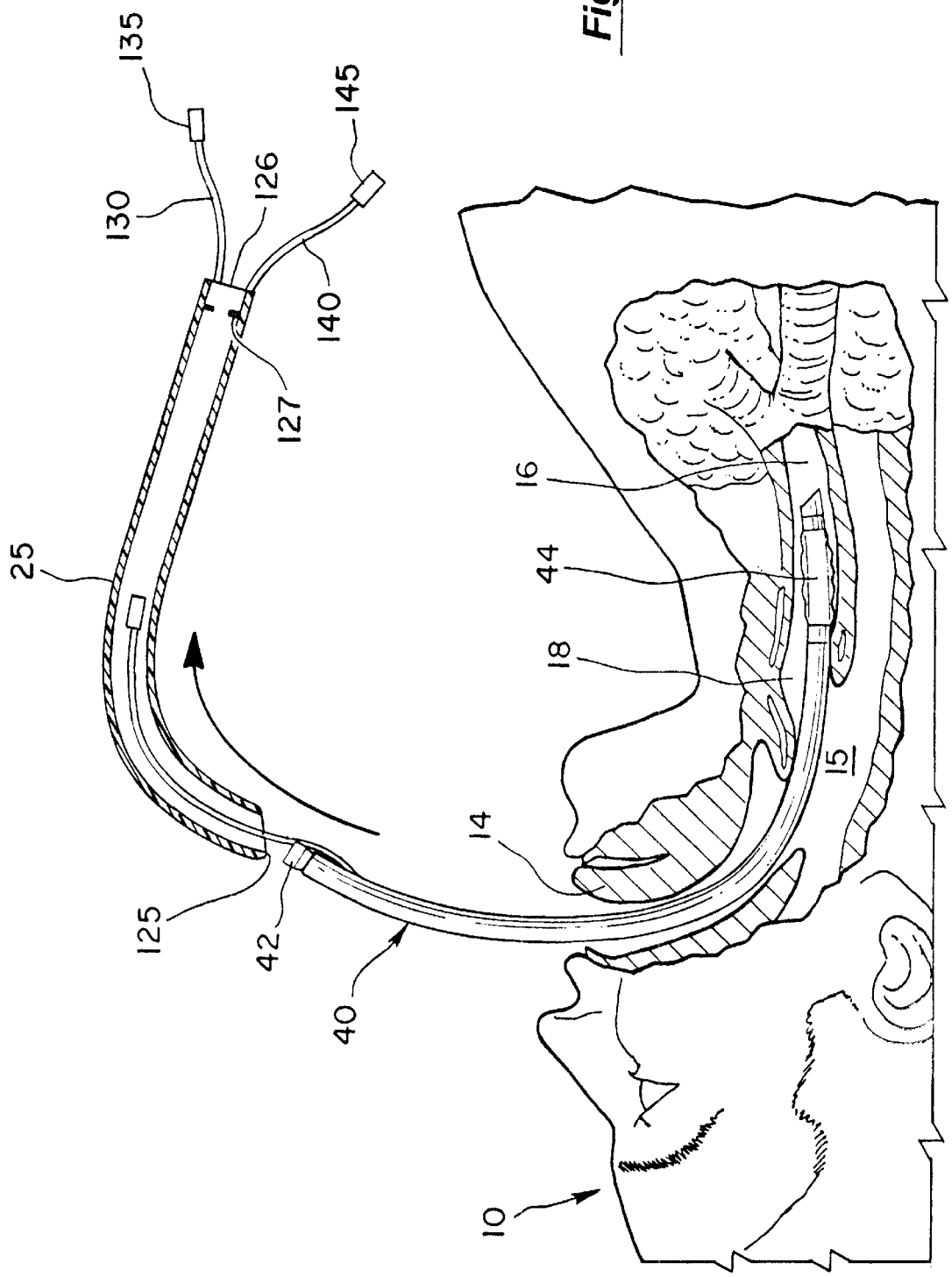
FIG. 6 is a cross-sectional view of the mouth and airway of the patient corresponding to FIG. 3 showing the guide assembly being removed while the endotracheal tube 40 remains in place.

The distal end 46 of the endotracheal tube 40 can be beveled as illustrated most clearly in FIG. 6. Experience has shown that injury to the larynx 18 can be reduced by spinning the endotracheal tube 40 as it is advanced. The beveled end tends to keep the endotracheal tube 40 centered as it is passes through the vocal cords. Injury to the lining of the mouth and trachea can be reduced by using an endotracheal tube 40 made of a material having a low coefficient of friction, such as silicone. Bivona Medical Technologies of Gary, Ind., markets a line of endotracheal tubes made of silicone with a helical reinforcing wire.

Figure 5:
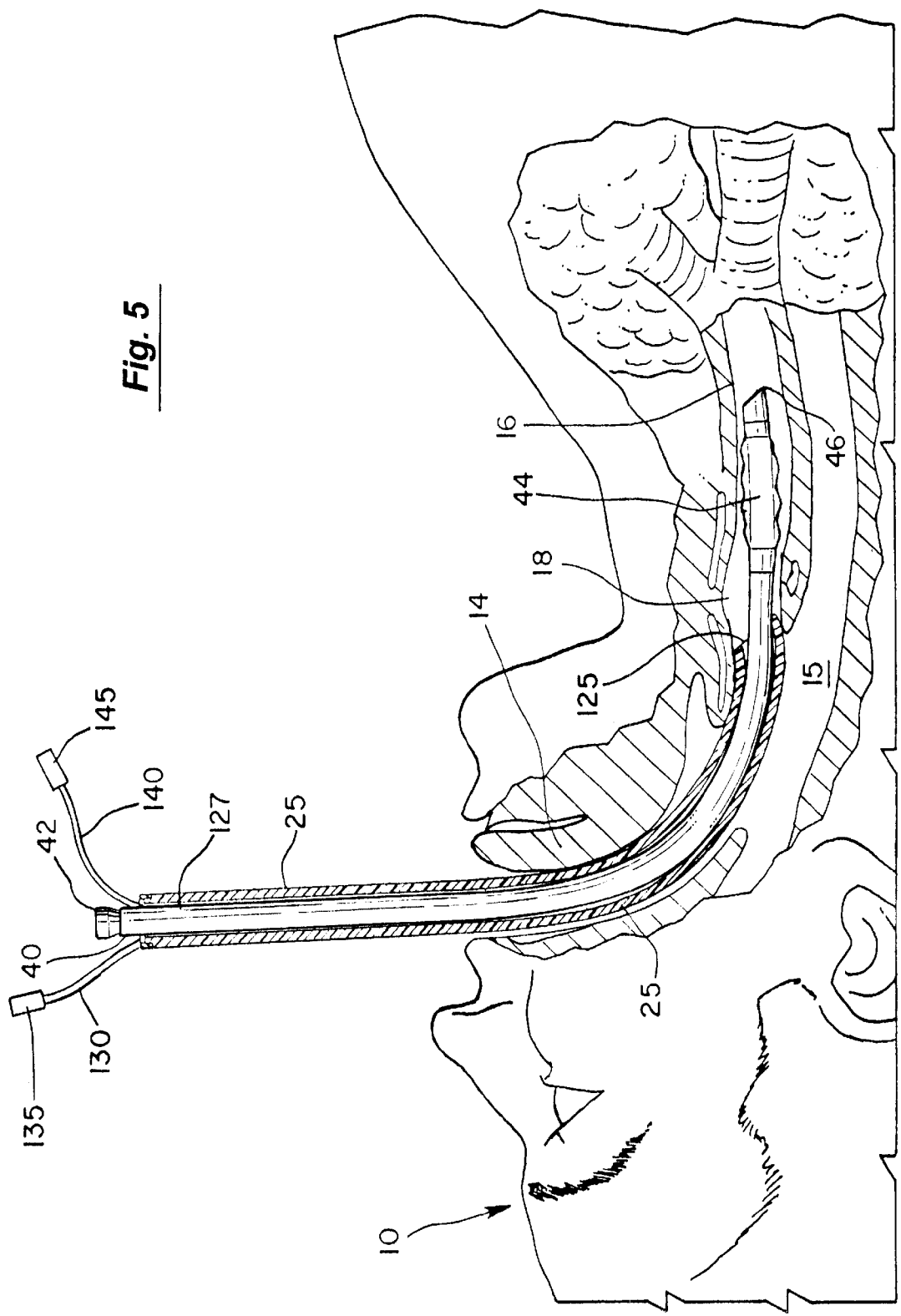
FIG. 5 is a cross-sectional view of the mouth and airway of the patient corresponding to FIG. 3 after the fiber optic probe 30 has been removed from within the endotracheal tube 40.

After the endotracheal tube 40 has been inserted, the fiber optic probe 30 is removed from within the endotracheal tube 40 through the proximal end of the endotracheal tube 40, as depicted in FIG. 5. The guide 25 can then be removed while leaving the endotracheal tube 40 in place within the trachea 16, as shown in FIG. 6. After the guide 25 has been removed, the endotracheal tube 40 is taped to the patient's face or held in place by some other suitable means for attachment. Alternatively, the guide 25 can be left in place to serve as an oral airway and to protect the endotracheal tube 40 from being bitten by the patient's teeth.

Figure 7:
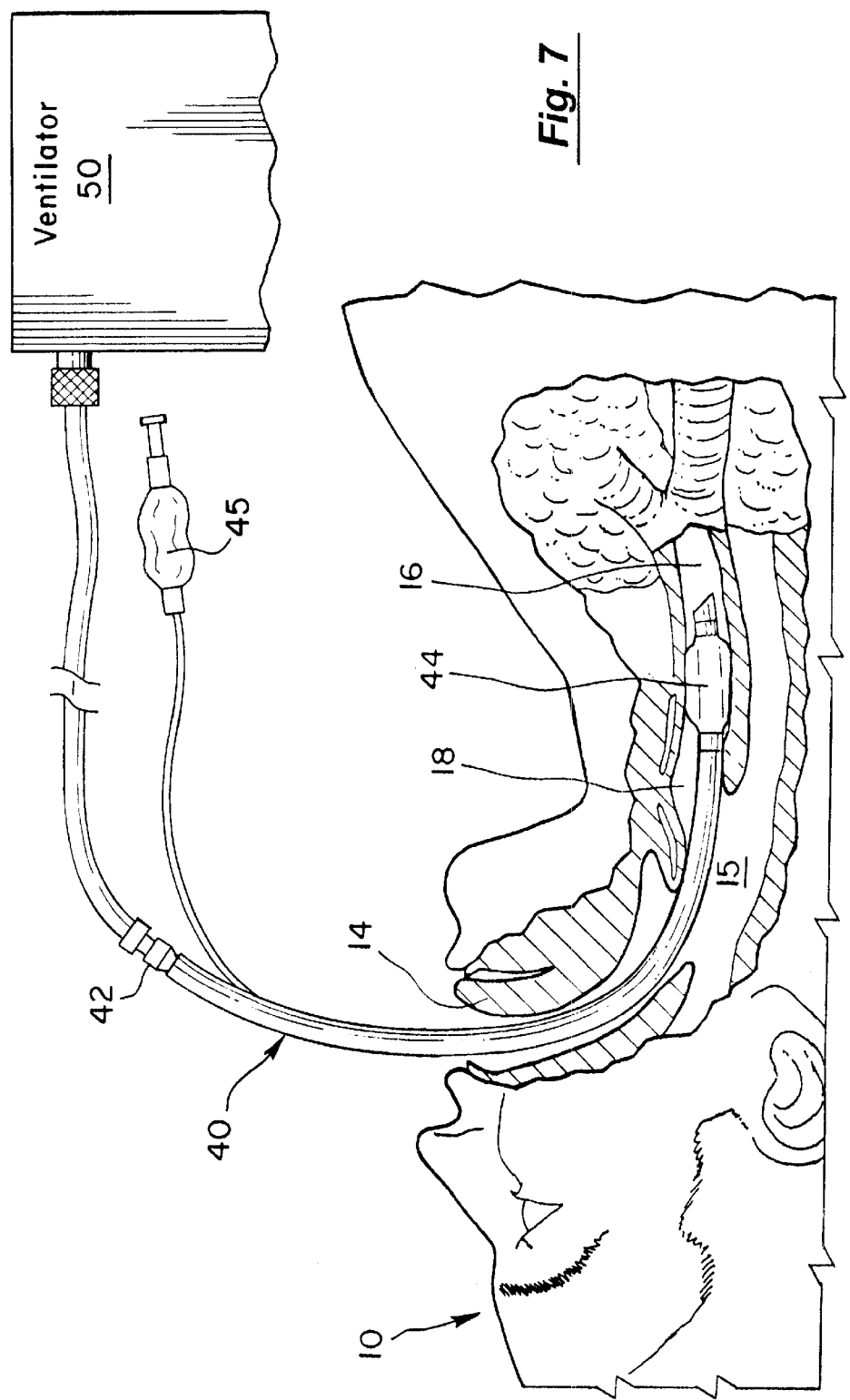
FIG. 7 is a cross-sectional view of the mouth and airway of the patient corresponding to FIG. 3 after the guide assembly has been removed, the endotracheal tube cuff 44 has been inflated, and a ventilator 50 has been connected to the endotracheal tube 40.

The cuff 44 at the distal end 46 of the endotracheal tube 40 is then inflated through the port valve 45 to block the trachea 16. An external ventilator 50 is then attached to the connector 42 at the proximal end of the endotracheal tube 40, as shown in FIG. 7. The patient can then be mechanically ventilated in the conventional manner via the endotracheal tube 40. Alternatively, the patient can be manually ventilated by attaching a resuscitation bag to the connector 42 at the proximal end of the endotracheal tube.

It is important to note that the present invention allows the guide 25 to be inserted while the patient's head remains in a neutral position. Many conventional intubation blades and laryngoscopes require that the patient's head must be tipped back, which can be dangerous or difficult for patients with head or neck injuries or arthritis. In contrast, the guide 25 in the present invention has a curved distal portion to fit the upper airway without tipping the patient's head back. It also can be used with a conventional endoscope, rather than requiring a dedicated fiber optic, due to the curvature of the guide 25. A conventional endoscope is often better when dealing with a difficult airway.

Face Mask

The present invention can either be used with or without a face mask. In an operating room environment, it is often advantageous for the anesthesiologist to be able to work with both hands if an assistant is not available. The previous embodiment of this invention enables the anesthesiologist to ventilate the patient, while keeping both hands free to perform endotracheal intubation. However, in an emergency setting, rapid resuscitation of the patient is often of paramount initial importance. Thus, a need exists for an embodiment of the present invention that incorporates a face mask to initially resuscitate the patient 10.

Figure 8:
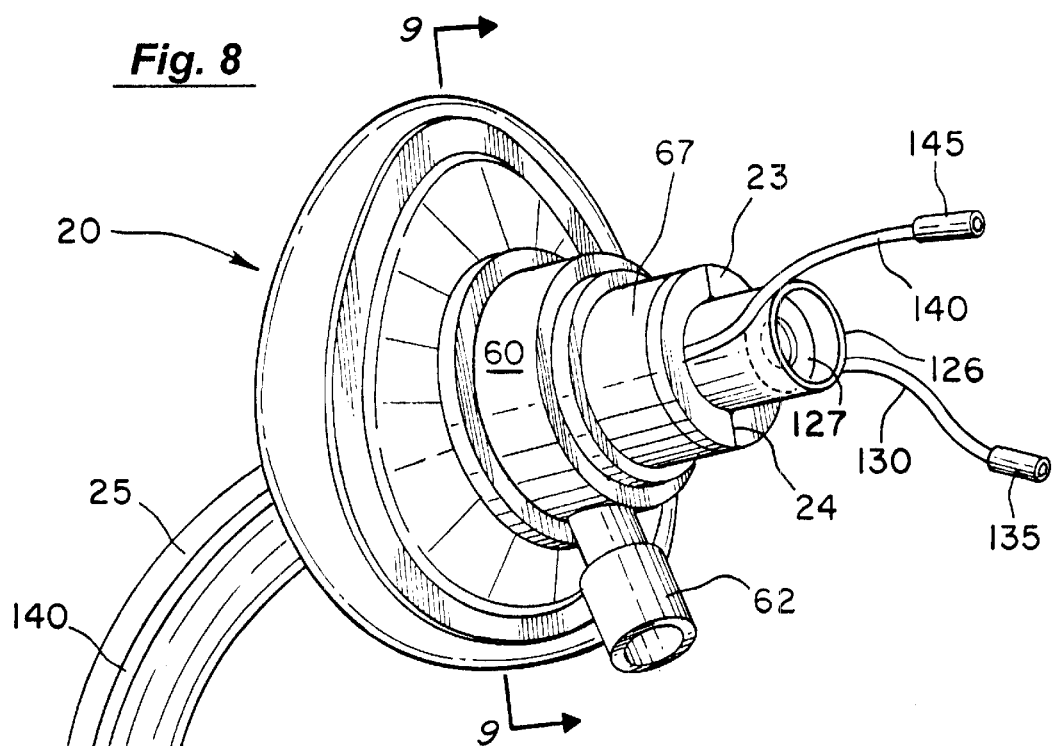
FIG. 8 is a front perspective view of an another embodiment of the guide assembly incorporating an face mask 20 for initial resuscitation of the patient.
Figure 9:
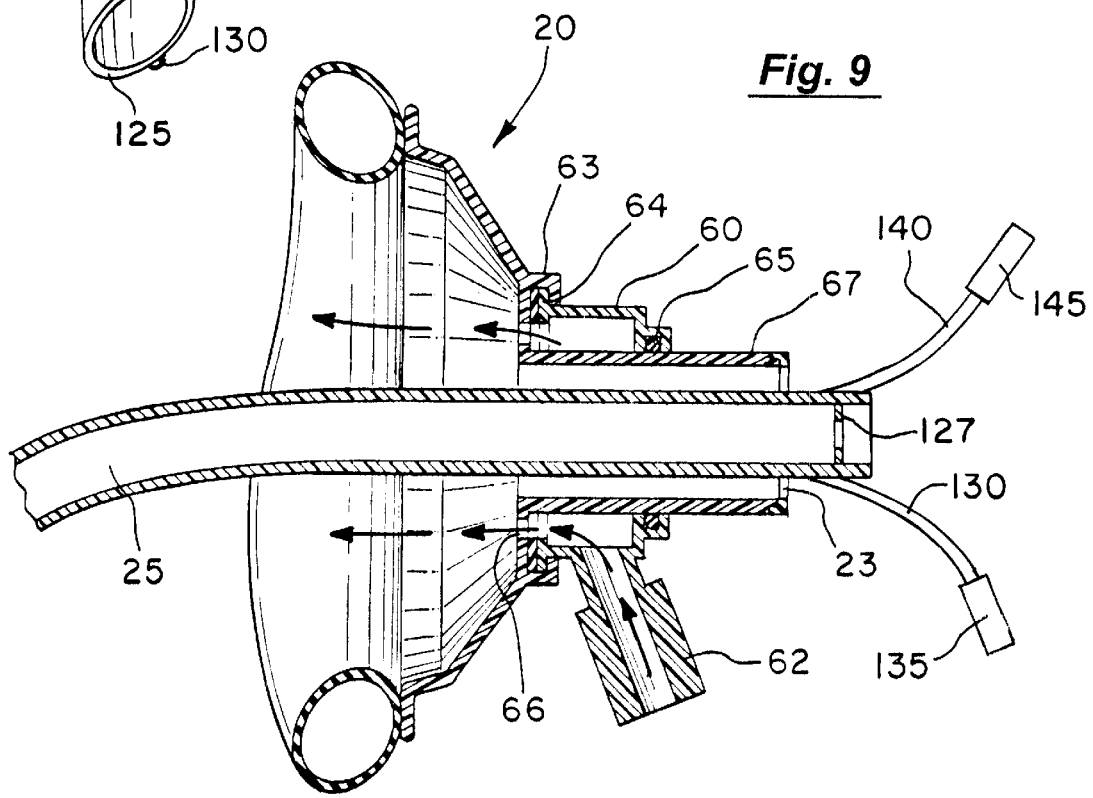
FIG. 9 is a cross-sectional view of the guide assembly and face mask corresponding to FIG. 8.
Figure 10:
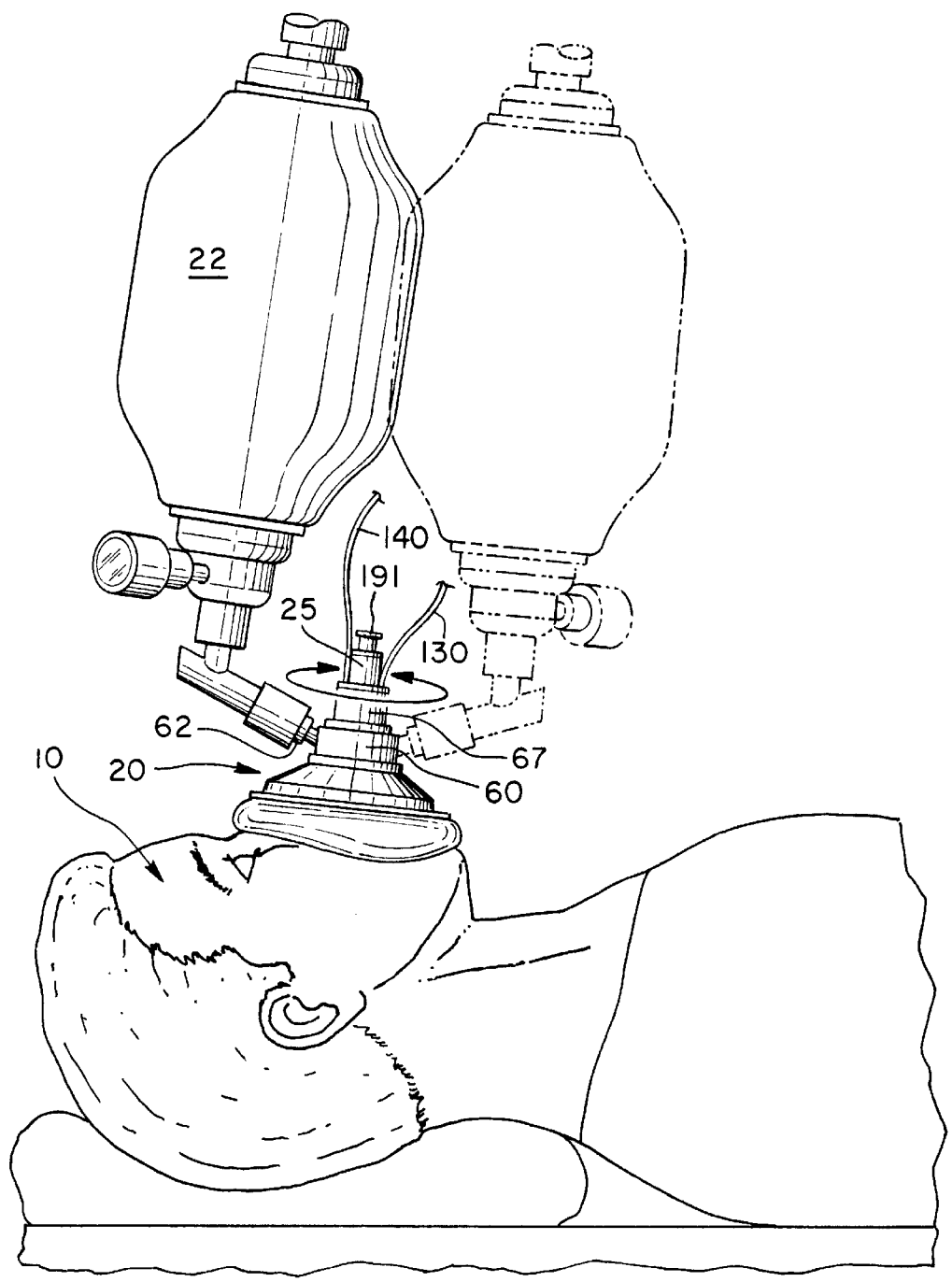
FIG. 10 is a side elevational view corresponding to FIGS. 8 and 9 showing the face mask 20 placed over the patient's mouth and nose.

FIGS. 8 through 10 show an embodiment of the present invention that includes a face mask 20. The face mask 20 is adapted to fit over the patient's mouth and nose for resuscitation of the patient 10 as shown in FIG. 10. The mask 20 has a low profile and is made of an elastic material, such as rubber or flexible plastic, to allow the mask to conform to the contours of the patient's face and create a more air-tight seal around the mouth and nose.

The face mask 20 includes a resealable port 23. In the preferred embodiment, the face mask port 23 consists of a flexible, elastic membrane having a stretchable opening 24 with dimensions large enough to allow the guide 25 to pass through the face mask port 23. For example, this elastic membrane can be made of rubber with slot or hole forming an opening 24, as shown in FIG. 4.

As depicted in FIG. 9, the guide 25 can be readily inserted through the face mask port 23 while maintaining a substantially air-tight seal around the guide 25 to prevent gas from escaping from within the face mask 20. The guide 25 extends posteriorly through the face mask 20 so that its curved distal portion is inserted into the patient's mouth and hypopharynx 15 as the face mask 20 is placed over the patient's mouth. The face mask port 23 allows the guide 25 to slide relative to the face mask 20, and also allows a limited range of rotation of the guide 25. This flexibility allows the guide 25 to accommodate a wide range of patient sizes and conditions.

For example, a flow of air can be supplied by a resuscitation bag 22 attached to the mask 20 that is manually squeezed periodically to simulate natural breathing, as illustrated in FIG. 10. However, other conventional air/oxygen supplies for resuscitation could be substituted at the resuscitation connector 62 for the face mask 20.

In the preferred embodiment, the flow of oxygen/air from the resuscitation bag 22 is directed around the exterior of the curved guide 25, as depicted in FIG. 9. This tends to inflate the patient's mouth and airway, which distends the collapsible tissues, and thereby makes visualization and insertion of the endotracheal tube 40 easier.

After the patient's condition has been stabilized to some degree during initial resuscitation, the guide cap 191 is removed, and the fiber optic probe 30 and endotracheal tube 40 are inserted through the guide 25 to a position within the trachea 16 past the larynx 18 while resuscitation continues, as previously discussed.

After the endotracheal tube 40 has been inserted, the fiber optic probe 30 is removed from within the endotracheal tube 40 through the proximal end of the endotracheal tube 40, as previously discussed. The face mask 20 and guide 25 can then be removed while leaving the endotracheal tube 40 in place within the trachea 16. The loose fit provided by the seal ring 127 within the proximal end of the guide 25 allows the face mask 20 and guide 25 to be withdrawn over the connector 42 at the proximal end of the endotracheal tube 40 with minimal effort and dislocation of the endotracheal tube 40. The position of the endotracheal tube 40 can be stabilized while the mask 20 is removed by manually gripping the proximal end of the endotracheal tube 40 and gradually urging it through the proximal end of the guide 25 as the mask 20 and guide 25 are lifted from the patient's face. The physician can then reach under the face mask 20 to grip the endotracheal tube 40 after the mask 20 and guide 25 have been lifted sufficiently to allow access. Alternatively, the face mask 20 can be removed while leaving the guide 25 in place to serve as an oral airway and to protect the endotracheal tube 40 from being bitten by the patient's teeth. The cuff 44 at the distal end 46 of the endotracheal tube 40 is then inflated through the port valve 45 to block the trachea 16 and a ventilator 50 is attached to the endotracheal tube 40, as previously discussed.

All of the components necessary to practice the present invention can be readily packaged as a kit for use in emergency rooms and intensive care units. The kit is sufficiently compact and inexpensive that it can be stocked on resuscitation carts widely used in hospitals, and carried in ambulances for use by emergency medical technicians in the field. The fiber optic probe can be operated using a battery-powered light source. The oxygen supply for the hospital or ambulance can be connected to the face mask 20 for resuscitation or to provide a flow of gas to the ventilator 50.

Rotatable Ventilation Port

The face mask assembly shown in FIG. 8 includes a rotatable ventilation port. FIG. 9 shows a cross-sectional view of the mask assembly. In contrast, many conventional face masks have a fixed ventilation port for connecting a resuscitation bag or other source of air/oxygen to the face mask. This limitation may present a significant problem in emergency situations in which only limited access to the patient is available, or in which the patient cannot be readily moved. Similar problems can also occur in a hospital setting, due to the patient's position in bed, or surrounding medical equipment that can limit access to the patient from one side or the other.

Returning to FIGS. 8–10, the mask assembly includes a rotatable annular ventilation collar 60 with a ventilation port 62 that can be connected to a conventional respiration bag 22 or other air/oxygen source to ventilate the patient. The ventilation collar 60 allows the ventilation port 62 to be freely rotated to any desired orientation about the face mask port 23. Air from the resuscitation bag 22 flows through the ventilation port 62 and into the annular ventilation collar 60. It then flows through a plurality of small ventilation holes 66 in the mask 20 beneath the annular ventilation collar 60 into the patient's mouth and nose. The resuscitation bag 22 is typically used to initially resuscitate the patient, and to provide short-term ventilation until the endotracheal tube 40 is in place and connected to a ventilator. After the patient has been intubated and connected to the ventilator, the resuscitation bag 22 can be removed. If needed, the resuscitation bag 22 can reconnected to the ventilation port 62 to supplement the flow provided by the ventilator.

In particular, the mask 20 includes a raised cylindrical flange 63 that engages a corresponding flange 64 extending around the base of the annular ventilation collar 60 to provide a rotatable, but generally air-tight seal between the mask 20 and the ventilation collar 60. A tubular member 67 extends upward from the surface of the mask 20 beneath the ventilation collar 60, and passes through the central opening in the annular ventilation collar 60. An O-ring 65 provides a rotatable, air-tight seal between the outer surface of the tubular member 67 and the ventilation collar 60, and also serves to retain the ventilation collar in place on the mask assembly 20.

A resealable face mask port 23 is provided at the upper opening of the tubular member 67, so that the guide 25 can be removably inserted through the face mask port 23 and into the patient's mouth and hypopharynx 15, as illustrated in FIG. 3. When the face mask port 23 is not in use (e.g., during initial resuscitation of a patient using the resuscitation bag 22), the face mask port 23 should remain sealed to prevent gas from escaping from the face mask 20. For example, the face mask port 23 can be a flexible membrane that has a stretchable opening to receive the guide 25. When the guide 25 is not inserted through the face mask port 23, the flexible membrane retracts to substantially seal the opening and prevent gas from escaping from the face mask port 23, as previously discussed. Alternatively, the face mask port 23 can be equipped with a removable cap to seal the port with it is not in use.

Resuscitation Attachment

FIG. 11 is a perspective view of a resuscitation attachment 70 that can used in place of the resuscitation bag 22 for mouth-to-mask resuscitation by the rescue person. In a hospital setting, the first person responding to a patient in need of resuscitation typically activates an alarm to summon a resuscitation team, and then immediately begins mouth-to-mouth resuscitation of the patient until the resuscitation team arrives. To help minimize the risk of contamination, many hospitals equip each hospital bed with a face mask having a ventilation port for mouth-to-mask resuscitation. This type of face mask is also commonly provided for use by police and firemen with little medical training. When the resuscitation team arrives, this face mask is generally replaced with a system consisting of a second face mask, an oral airway, and a resuscitation bag. Since the patient usually requires intubation, this second face mask must be removed while an endotracheal tube is inserted into the patient's airway and the patient is connected to a ventilator. Each of these transitions entails an interruption in on-going resuscitation efforts, which can be detrimental to the patient. According to the American Heart Association, a period in excess of 30 seconds without breathing or circulation can cause irreversible brain and heart damage.

In addition, the most common types of face masks used for initial resuscitation at the patient's bed do not include a guide or oral airway to keep the patient's airway open. As a result, initial efforts at manual resuscitation using the first face mask may be partially or completely ineffective, until the resuscitation team arrives and replaces the first face mask with a second face mask and a separate airway device used to keep the patient's airway open.

In contrast to the conventional approach practiced in many hospitals, as described above, the present invention allows the same face mask to be used throughout the entire process without interrupting resuscitation. In addition, the present invention includes a face mask 20 with a curved guide 25 that can be inserted into the patient's airway to maintain patency during the first effort to resuscitate the patient before the resuscitation team arrives.

Returning to FIG. 11, the resuscitation attachment 70 has an output port 71 that can be removably connected to the ventilation port 62 of the face mask 20. The healthcare provider administers mouth-to-mask resuscitation to the patient via the resuscitation attachment 70 and face mask 20.

The resuscitation attachment 70 includes an air filter 74 across the flow path between the input port 72 and output port 71, to help prevent the exchange of contaminants between the healthcare provider and patient. A one-way valve 75 (e.g., a duckbill valve) directs any backflow of air or contaminated fluids from the face mask 20 to the exhaust port 73, and thereby serves to further protect the healthcare provider from contaminants.

The healthcare provider can breathe directly into the input port 72 of the resuscitation attachment 70. Alternatively, a length of flexible tubing 80 can be connected to the resuscitation attachment 70 by means of a connector 82 that can be plugged into the input port 72 of the resuscitation attachment 70, as shown in FIG. 12. In the preferred embodiment, the flexible tubing 80 is approximately six inches in length and forms a helical coil for easier storage. The proximal end of the flexible tubing 80 has a mouthpiece 84 with an oval opening.

The resuscitation attachment 70 can also be equipped with an oxygen port 76, as shown in FIG. 12, that can be connected by tubing to a external oxygen source to supply supplemental oxygen to the patient through the flow path, in addition to the mouth-to-mask resuscitation provided by the healthcare provider. Each exhalation by the healthcare provider then carries oxygen-enriched air through the face mask 20 and into the patient's lungs. The oxygen port 76 can be closed with a removable cap 77 when the oxygen port 76 is not in use. The internal passageway within the flexible tubing 80 and resuscitation attachment 70 upstream from the one-way valve 75 serve as a reservoir for accumulation of oxygen between each exhalation by the healthcare provider.

FIG. 13 shows an alternative embodiment of the resuscitation attachment 70 with the oxygen port 76 placed below the one-way valve 75 and filter 74. In this embodiment, the internal passageway within the resuscitation attachment 70 downstream from the one-way valve 75 serves as a reservoir for accumulation of oxygen between each exhalation by the healthcare provider. The one-way valve 75 helps to prevent oxygen from escaping during the remainder of the resuscitation cycle. However, the exhalation port 73 prevents the build-up of excessive pressure that might be injurious to the patient's lungs.

Removable Guide Cap

Figure 14:
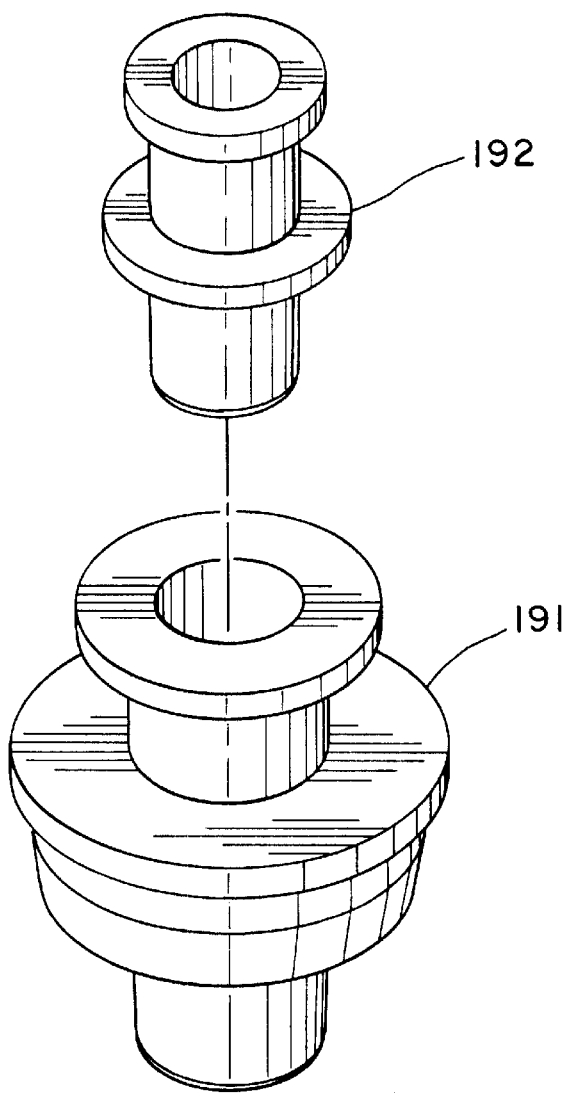
FIG. 14 is an exploded perspective view of the guide cap assembly.
Figure 15:
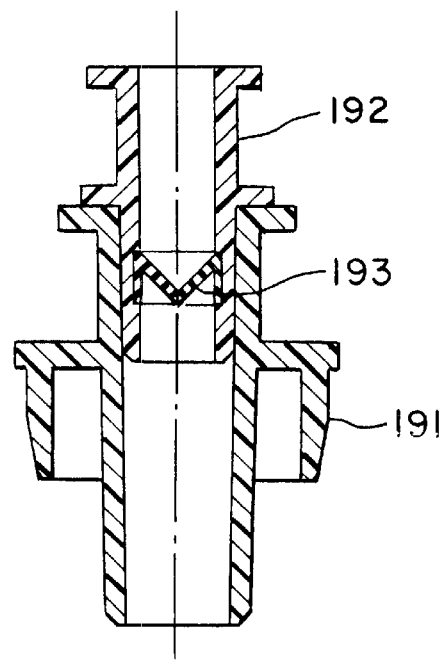
FIG. 15 is a cross-sectional view of the guide cap assembly corresponding to FIG. 14.
Figure 16:
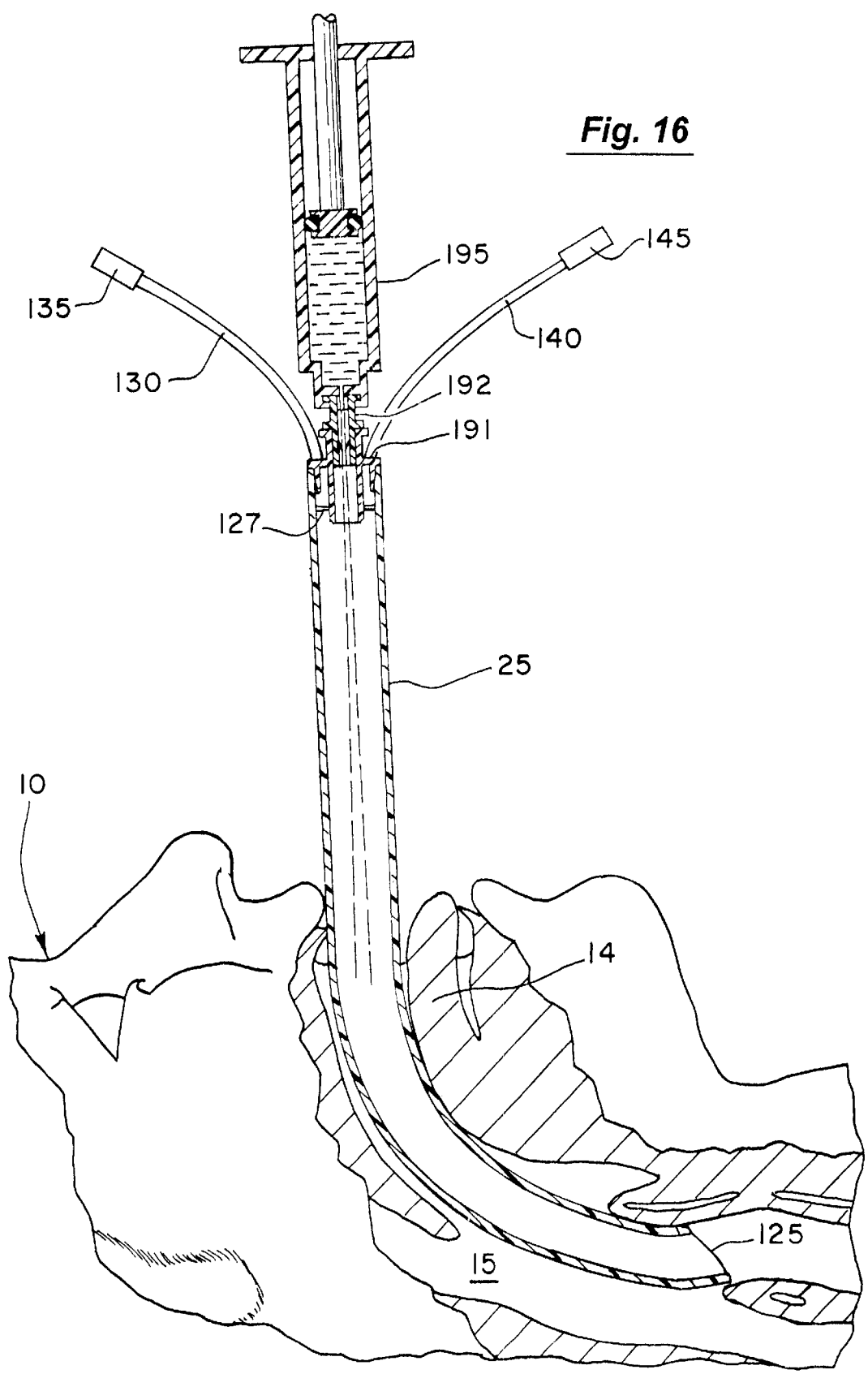
FIG. 16 is a cross-sectional view of a patient's mouth and airway illustrating the manner in which a local anesthetic can be administered from a syringe 195 while the guide 25 is advanced along the patient's airway.

FIGS. 14–16 show a removable cap assembly that can be used to seal the proximal end of the guide 25. As shown in the exploded perspective view of the cap assembly provided in FIG. 14, the guide cap 191 has an outside diameter dimensioned to seat into the proximal opening of the guide 25. A central passageway extends through the guide cap 191. As shown in the cross-sectional view provided in FIG. 15, a luer connector 192 with a one-way valve 193 (e.g., a duck-bill valve) is permanently attached to the guide cap 191 so that air or fluid can only flow down the passageway of the guide cap 191, but not up. Thus, the one-way valve 193 serves to prevent air/oxygen from escaping through the guide 25 during initial resuscitation.

As illustrated in the cross-sectional view provided in FIG. 16, a syringe 195 containing anesthetic can be secured to the luer connector 192 on the guide cap 191. As the guide 25 is advanced into the patient's mouth and hypopharynx, the healthcare provider squirts anesthetic from the syringe 195, through the one-way valve 193 and guide 25 to lessen discomfort. After the guide 25 has been advanced into position, the guide cap 191 is removed from the guide 25 to allow insertion of the endotracheal tube 40 and fiber optic probe 30 through the guide 25, as previously discussed.

Fiber Optic Probe Stabilizer

Figure 17:
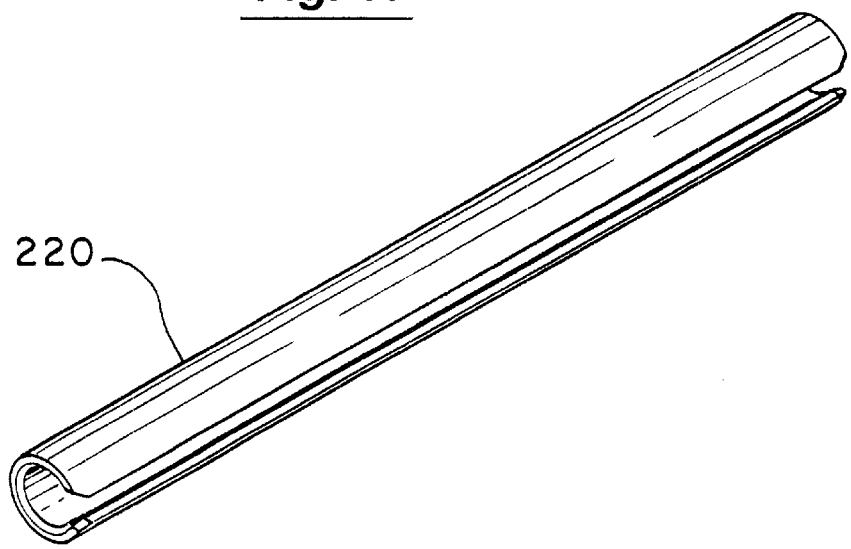
FIG. 17 is a perspective view of the stabilizer 220 that can attached to the fiber optic probe of an endoscope.
Figure 18:
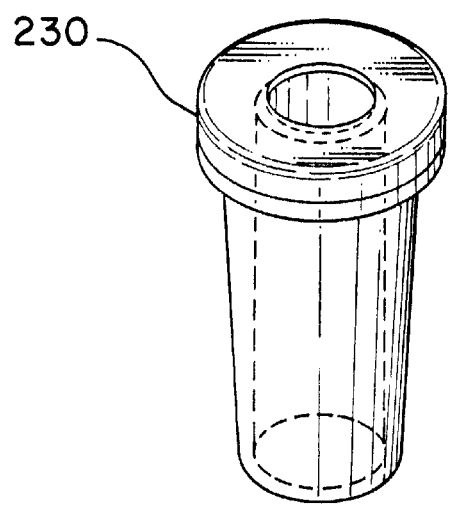
FIG. 18 is a perspective view of the endotracheal tube cap 230 that can be used in conjunction with a stabilizer 220.
Figure 19:
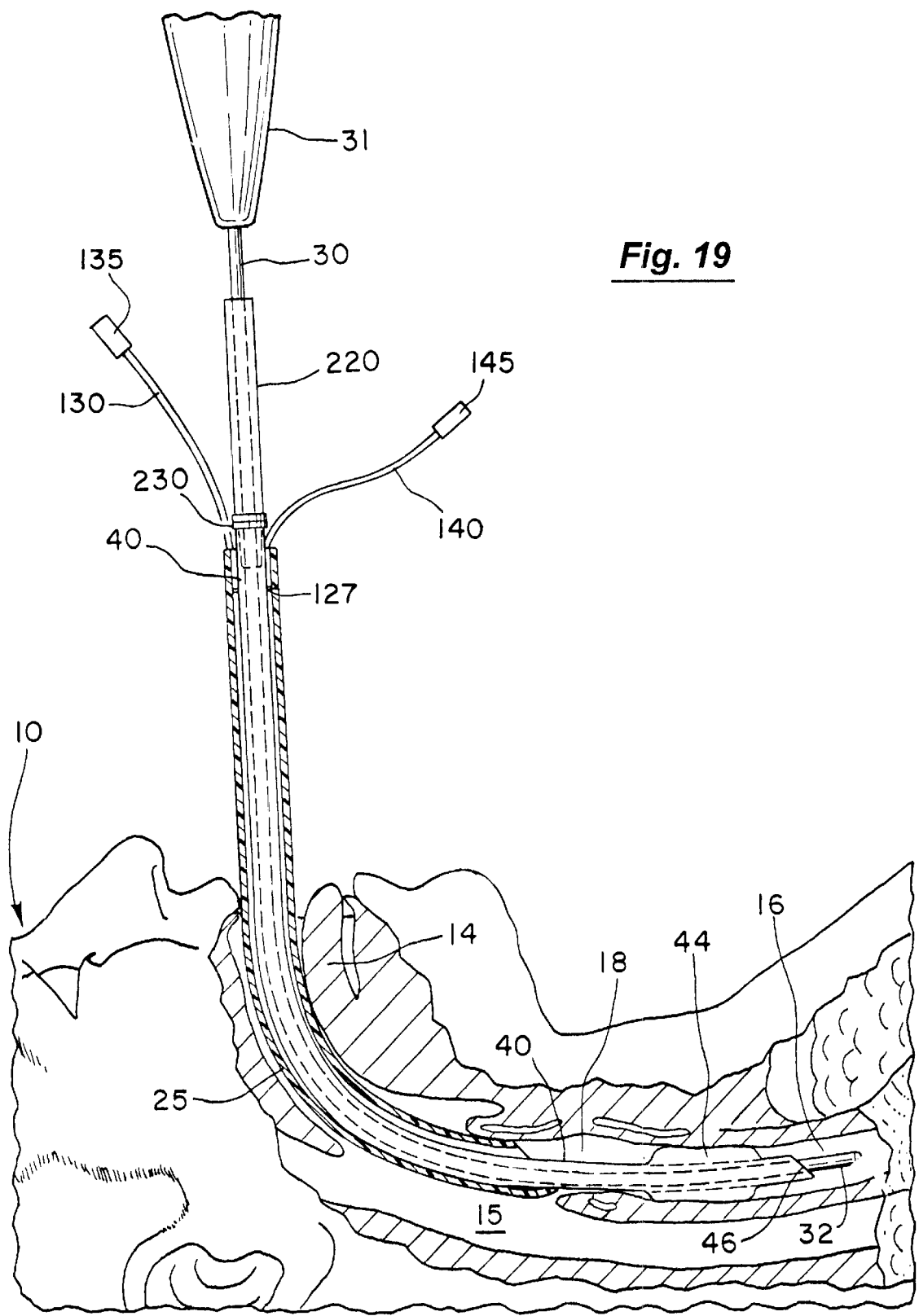
FIG. 19 is a cross-sectional view of a patient's mouth and airway showing how the stabilizer 220 and endotracheal tube cap 230 can be used to advance the endotracheal tube 40 through the guide 25 to a position below the larynx 18.

FIGS. 17–19 show another embodiment in which a stabilizer 220 is attached to the endoscope probe 30 and then used to advance the endotracheal tube 40 along the guide 25 and into the patient's trachea. In the preferred embodiment, the stabilizer 220 is a flexible plastic tube having a C-shaped cross-section, as shown in FIG. 17, that can be readily clipped over the fiber optic probe 30 at any desired location along its length.

The inside diameter of the stabilizer 220 should be selected to provide a snug, frictional fit against the exterior of the fiber optic probe 30 so that the stabilizer 220 will not readily slide after it has been attached to the fiber optic probe 30. The stabilizer 220 can also be readily removed from the endoscope probe 30 by the healthcare provider for cleaning or to adjust its location on the probe 30. The stabilizer 220 should have outside dimensions sufficiently large to push the endotracheal tube forward as the fiber optic probe 30 is advanced by the healthcare provider.

The proximal end of the endotracheal tube 40 can be fitted with a removable cap 230 shown in FIG. 18. This cap 230 has outside dimensions selected so that it can be inserted snugly into the proximal opening of the endotracheal tube 40 and yet is sufficiently small to fit through the guide 25, if necessary.

A central passageway extends axially through the cap 230 to receive the fiber optic probe 30. The fiber optic probe 30 passes freely through the cap 230. However, the cap passageway has an inside diameter smaller than the stabilizer 220, so that the stabilizer 220 will abut and push against the proximal end of the endotracheal tube 40 as the fiber optic probe 30 is advanced by the healthcare provider.

In practice, this embodiment of the present invention typically uses the following sequence of steps. If a face mask 20 is being used, it is placed over the patient's mouth and the patient is initially resuscitated by a flow of air/oxygen delivered through the face mask ventilation port 62. With the guide cap 191 sealing the proximal end of the guide 25, the distal portion of the guide 25 is advanced by the healthcare provider into the patient's mouth and hypopharynx, as previously discussed. If necessary, a syringe 195 can be attached to the guide cap 191 to spray anesthetic down the guide 25 and into the patient's airway to less discomfort.

The stabilizer 220 is attached at a desired position on a fiber optic probe 30 of the endoscope. The fiber optic probe 30 is then inserted into the proximal end of the endotracheal tube 40 until the stabilizer 220 abuts the proximal end of the endotracheal tube 40. The location of the stabilizer 220 on the fiber optic probe 30 is normally selected so that the distal tip of the fiber optic probe 30 will extend slightly beyond the distal tip 46 of the endotracheal tube 40.

Optionally, a removable endotracheal tube cap 230 is attached to the proximal end of the endotracheal tube 40 prior to insertion of the fiber optic probe 30 so that the stabilizer 220 will push against this cap 230 as the healthcare provider advances the fiber optic probe 30. In this variation, the fiber optic probe 30 is inserted through both the endotracheal tube cap 230 and the endotracheal tube 40.

The guide cap 191 and syringe 195 are removed from the guide 25, and the assembly consisting of the endotracheal tube 40, fiber optic probe 30 and stabilizer 220 is inserted through the proximal end of the guide 25. The healthcare provider then pushes forward on the fiber optic probe 30 to advance the endotracheal tube 40 and the fiber optic probe 30 along the guide 25 and into the patient's trachea 16 as shown in FIG. 19. If the fiber optic probe 30 is part of a conventional endoscope, the healthcare provider can view through the endoscope probe 30 and manipulate the controls on the endoscope housing 31 to navigate the distal portion of the endotracheal tube 40 through the pharynx and into the larynx. Many conventional endoscopes include a suction channel extending the length of the fiber optic probe to its distal tip. This feature can be used to suction mucus or other secretions from the patient's airway as the endoscope/endotracheal tube assembly is inserted.

After the endotracheal tube 40 has been moved into position with its distal end in the trachea, the face mask 20 and guide 25 are removed over the proximal end of the endotracheal tube 40 while leaving the endotracheal tube 40 and fiber optic probe 30 in place. More specifically, the face mask 20 and guide 25 can either be removed together, or the face mask 20 can be removed first followed by the guide 25.

Before removing the face mask 20 and guide 25, the healthcare provider may wish to slide the stabilizer 220 a few centimeters toward the distal end of the fiber optic probe 30. This allows the endoscope to be pulled back relative to the endotracheal tube 40, so that the distal tip of the endoscope is located within the distal end of the endotracheal tube 40 and offers a view of both the endotracheal tube's distal tip and the patient's trachea. This enables the healthcare provider to monitor the position of the endotracheal tube 40 relative to the trachea as the face mask 20 and guide 25 are removed, as described above.

The fiber optic probe 30 is then withdrawn from within the endotracheal tube 40 and the endotracheal tube cap 230 is removed if one is present. Finally, the patient can be ventilated via a conventional ventilator connected to the endotracheal tube 40.

The above disclosure sets forth a number of embodiments of the present invention. Other arrangements or embodiments, not precisely set forth, could be practiced under the teachings of the present invention and as set forth in the following claims.

I claim:

1. An apparatus for guiding insertion of an endotracheal tube into a patient's trachea while ventilating the patient, said apparatus comprising:
    a tubular guide having a main lumen to direct insertion of an endotracheal tube through the guide into a patient's trachea;
    said guide having a curved distal portion for insertion into a patient's mouth and hypopharynx to a position adjacent to the patient's larynx, and a proximal end extending out of the patient's mouth;
    a second lumen extending along the guide to supply air/oxygen into the patient's lungs through the larynx;
    a guide cap removably insertable onto the proximal end of the guide having:
        (a) a guide cap passageway extending through the guide cap; and
        (b) a one-way valve allowing anesthetic to be introduced through the guide cap passageway and guide during insertion of the guide into the patient's mouth and hypopharynx, but substantially preventing patient secretions from passing through the guide during resuscitation of the patient, said guide cap being removable from the guide to allow insertion of the endotracheal tube through the guide;
    a fiber optic probe insertable through an endotracheal tube; and
    a stabilizer removably attachable to the fiber optic probe, said stabilizer having dimensions sufficiently large to push the endotracheal tube forward as the fiber optic probe is advanced along the guide and into the patient's trachea.

2. The apparatus of claim 1 wherein the second lumen extends along a lateral portion of the guide.

3. The apparatus of claim 1 further comprising a face mask to cover a patient's mouth having a face mask port to receive the guide, and a ventilation port allowing a flow of air/oxygen into the face mask to resuscitate the patient.

4. The apparatus of claim 3 wherein the guide further comprises a annular ring within the proximal end of the guide forming a seal around the endotracheal tube.

5. The apparatus of claim 1 wherein air/oxygen is delivered through the second lumen at a flow rate of approximately 1 to 20 liters per minute.

6. The apparatus of claim 1 wherein the guide is substantially J-shaped.

7. The apparatus of claim 1 further comprising a third lumen extending along the guide for measurement of a concentration of carbon dioxide in the patient's airway.

8. An apparatus for guiding insertion of an endotracheal tube into a patient's trachea while ventilating the patient, said apparatus comprising:
    a tubular guide having a curved distal portion for insertion into a patient's mouth and hypopharynx with a main lumen to direct insertion of an endotracheal tube into the patient's trachea;
    a fiber optic probe insertable through an endotracheal tube;
    a stabilizer removably attachable to the fiber optic probe, said stabilizer having dimensions sufficiently large to push the endotracheal tube forward as the fiber optic probe is advanced along the guide and into the patient's trachea; and
    a second lumen extending along the guide to supply air/oxygen into the patient's lungs through the patient's larynx.

9. The apparatus of claim 8 further comprising an endotracheal tube cap removably attachable to proximal end of the endotracheal tube having a passageway to receive the fiber optic probe.

10. The apparatus of claim 9 wherein the passageway of the endotracheal tube cap has an inside diameter smaller than the stabilizer.

11. The apparatus of claim 8 wherein the stabilizer comprises a flexible tube having a C-shaped cross-section.

12. The apparatus of claim 8 wherein the fiber optic probe is an endoscope probe and wherein said stabilizer can be attached to any point along the endoscope probe.

13. A method for resuscitating a patient and guiding insertion of an endotracheal tube into the patient's trachea comprising:
    inserting a tubular guide into a patient's mouth and hypopharynx, said guide having a main lumen and a curved distal portion shaped to allow insertion of an endotracheal tube through the guide into a patient's trachea, said guide further having a second lumen extending along the guide;
    inserting the fiber optic probe into an endotracheal tube;
    advancing the fiber optic probe and endotracheal tube so that the endotracheal tube advances along the guide and into the patient's trachea;
    supplying air/oxygen via the second lumen into the patient's lungs while advancing the endotracheal tube and fiber optic probe;
    removing the guide from the endotracheal tube;
    removing the fiber optic probe from the endotracheal tube; and
    ventilating the patient through the endotracheal tube.

14. The method of claim 13 further comprising the steps of:
    attaching a stabilizer at a desired position on the fiber optic probe; and
    inserting the fiber optic probe into the endotracheal tube until the stabilizer abuts the proximal end of the endotracheal tube.

15. The method of claim 14 wherein the stabilizer is attached to the fiber optic probe at a location so that the distal tip of the fiber optic probe extends beyond the distal tip of the endotracheal tube.

16. The method of claim 14 further comprising the steps of:
    attaching a removable cap to the proximal end of the endotracheal tube prior to insertion of the fiber optic probe, said cap having a passageway to receive the fiber optic probe with an inside diameter larger than the stabilizer; and
    removing the cap from the endotracheal after the fiber optic probe is removed from the endotracheal tube and prior to ventilating the patient through the endotracheal tube.

17. The method of claim 13 wherein air/oxygen is supplied through the second lumen at a flow rate of approximately 1 to 20 liters per minute.

\* \* \* \* \*